(12) United States Patent
Frey

(10) Patent No.: US 8,247,348 B1
(45) Date of Patent: Aug. 21, 2012

(54) METHOD OF PRESERVING CUT PLANT MATERIAL

(76) Inventor: Steven J Frey, Dearborn Heights, MI (US)

( * ) Notice: Subject to any disclaimer, the term of this patent is extended or adjusted under 35 U.S.C. 154(b) by 1198 days.

(21) Appl. No.: 11/890,967

(22) Filed: Aug. 8, 2007

(51) Int. Cl.
*A01N 3/02* (2006.01)

(52) U.S. Cl. ..................................................... 504/114

(58) Field of Classification Search .................. None
See application file for complete search history.

(56) References Cited

U.S. PATENT DOCUMENTS

| | | | |
|---|---|---|---|
| H950 H | * | 8/1991 | O'Brien et al. ............... 426/639 |
| 6,808,729 B1 | * | 10/2004 | Roselle et al. ............... 426/326 |
| 7,345,008 B1 | * | 3/2008 | Suzuki et al. ............... 504/114 |

* cited by examiner

*Primary Examiner* — Johann Richter
*Assistant Examiner* — Thor Nielsen

(57) ABSTRACT

The present invention is directed to a composition of matter to be applied to a carved pumpkin, more commonly called a jack o'lantern, in order to retard environmental degradation thereof, and to repel insects. The composition consists of an aqueous solution containing an antiseptic, a fungicide, an insecticide and a desiccant. The carved pumpkin is totally immersed in the aqueous solution to create a hyperosmotic condition to allow the preservative solution to permeate the fibers of the carved pumpkin, and at the same time replacing moisture from within the carved pumpkin with a mineral, to retain the original shape and structural stability of the carved pumpkin. The composition may also contain a buffer to maintain a pH level above 8.0. The present invention also provides a method of protecting a carved pumpkin using a composition according to the present invention.

6 Claims, No Drawings

METHOD OF PRESERVING CUT PLANT MATERIAL

RELATED APPLICATIONS

The present application is related to U.S. Pat. No. 6,099,892, issued Aug. 8, 2000, for PROTECTIVE COATING FOR DECORATIVE VEGETABLE MATERIAL, included by reference herein.

FIELD OF THE INVENTION

The present invention relates to a composition of matter and method of application to preserve carved pumpkins, more commonly called jack o'lanterns.

BACKGROUND OF THE INVENTION

When the term "Jack O'Lantern" first appeared in print in 1750, it referred to a night watchman or a man carrying a lantern. This was based on an Irish folk legend about a man named Jack who was forced to wander in the darkness until "Judgment Day", thus becoming known as the symbol of a damned soul. At the time, people believed that spirits and ghosts left the grave on Halloween and would seek out warmth in their previous homes. Villagers, fearful of the possibility of being visited by the ghosts of past occupants, would dress up in costumes to scare the spirits on their way. They would also leave food and other treats at their door to appease the spirits, so they would not destroy their homes or crops, but instead move on down the road. They also began to hollow out turnips with a face either painted or carved into it, and placed lighted candles inside, hoping the image of a dammed soul would scare the spirits away.

The Irish Potato Famine (1845-50) prompted over 700,000 men, women and children to immigrate to the Americas. These immigrants brought with them their traditions of Halloween and Jack O'Lanterns, but turnips were not as readily available in the United States as in Ireland. They found however, the American pumpkin to be a more than adequate replacement. Today, the carved pumpkin is perhaps the most recognizable icon of the holiday, and carving a pumpkin is one of the most popular activities of the season, enjoyed by families and people of all ages.

Traditionally, pumpkin carving involves the removal of a portion of the pumpkin shell surrounding the stem, removal of the seeds and fibers contained in the pumpkin and carving humorous, grotesque or other decorative features in the pumpkin shell by removing fleshy portions of the shell to obtain the desired appearance. Internal illumination is then provided by a candle or electric light. This illumination results in a glowing decorative pattern.

Carved pumpkins are often placed on display indoors or outdoors during the days surrounding Halloween. It is generally desired that such a carved pumpkin will maintain its appearance for a significant time period. One problem with preserving the appearance of a carved pumpkin is that, over time, the fleshy shell of a carved pumpkin will degrade from the effects of environmental factors acting upon it. A carved pumpkin may dry out over time, causing the shell to shrink and the design carved therein to become warped. Mildew, mold and fungus may begin to grow thereupon, causing further degradation and an unsightly appearance, as well as creating difficulties in disposing of the degraded pumpkin shell. Because pumpkins are a fruit, they will attract insects when cut and stored outdoors. Further, outdoor temperature fluctuations can cause periodic freezing and thawing of the water contained in the pumpkin shell, which can rapidly break down cell material, causing additional degradation and detriment to the appearance of the carved pumpkin. It should be noted that other vegetables (such as squash), as well as fruit, which may also be hollowed out and carved into decorative configurations, can be subject to similar environmental degradation.

An attempt to solve the problem of carved pumpkin degradation is found in the "Pumpkin Fresh" product, produced by Large Marketing, PO Box 871211, Vancouver, Wash. 98687 and "PROTECTIVE COATING FOR DECORATIVE VEGETABLE MATERIAL", U.S. Pat. No. 6,099,892.

The Pumpkin Fresh product contains sodium benzoate and purports to be an fungicidal solution. Sodium benzoate is fungistatic not fungicidal, and is effective only in acidic conditions (pH<4.5). See O. Padilla-Zakour, Chemical Food Preservatives: Bonzoate & Sorbate, Venture, NYS Food Venture Center, Summer 1998•Vol. 1 No. 2. The Pumpkin Fresh product is slightly alkaline (pH 8.2), thus nullifying the effectiveness of the sodium benzoate. Furthermore, the product does not offer any protection from shriveling or other geometric distortions due to dehydration.

To attempt to retard the growth of mold and other fungi, U.S. Pat. No. 6,099,892, "PROTECTIVE COATING FOR DECORATIVE VEGETABLE MATERIAL", contains the chemical fungicide 3-iodo-2-propynyl butyl carbamate, which is a proven carcinogen, as well as a reproductive, developmental and neurological toxin. See S. Kegley, B. Hill, S. Orme, PAN Pesticide Database, Pesticide Action Network, North America (San Francisco, Calif. 2007).

U.S. Pat. No. 6,099,892 also contains ethylene glycol to prevent freezing, and due to its sweet taste, children and animals will sometimes consume large quantities of it if given access. Ethylene glycol is highly toxic with an estimated LD100 in humans of approximately 1.4 ml/kg. See J. Brent, Current management of ethylene glycol poisoning, Drugs, 61 (7): 979-88, PMID 11434452. However, as little as 30 milliliters (2 tablespoons) can be lethal to adults. See D. Field, Acute ethylene glycol poisoning, Crit Care Med 13 (10): 872-3, PMID 4028762.

To attempt to preserve a carved pumpkin's shape, U.S. Pat. No. 6,099,892 incorporates a film former of styrene acrylic resin to create a vapor barrier to trap moisture inside the flesh of the pumpkin. This trapped moisture actually promotes decay, rather than prevent it. The ancient Egyptians realized this centuries ago, which is why they chose to preserve their mummies by removing moisture, not sealing it in. Bacteria, decay mold and decay fungi are present in almost all organic materials. When moisture and a food source (namely the carved pumpkin) become available they will multiply rapidly and quickly break down the pumpkin.

Also, U.S. Pat. No. 6,099,892 offers no protection against insect infestation, which depending on geographic and weather conditions, can have devastating results.

Both of these above mentioned solutions are inherently flawed by their method of application. In both cases, the preservative solution is applied by spraying a thin coat of the product to the exterior of the pumpkin. While this method may offer limited protection to the outside of the pumpkin, they do not offer any protection to the plant material below the surface.

Accordingly, it is desirable to provide a relatively safe and efficient method of retarding environmental degradation and insect infestation of the entirety of carved pumpkins. There is thus a need in the industry for a relatively safe and effective composition and method for treating carved pumpkins which are operative to retard environmental degradation and insect infestation thereof. The present invention satisfies these needs and provides these benefits.

It is therefore an object of the invention to prevent shriveling, collapse or other geometric distortions of the desired shape of a carved pumpkin.

It is another object of the invention to retard decomposition of a carved pumpkin.

It is another object of the invention to retard microbial and fungi growth on the carved pumpkin.

It is another object of the invention to repel insects away from a carved pumpkin.

It is another object of the invention to provide a method for treating a carved pumpkin with preservative solution.

SUMMARY OF THE INVENTION

In accordance with the present invention, there is provided a method for retarding environmental degradation and insect infestation of carved pumpkins.

DESCRIPTION OF THE PREFERRED EMBODIMENT

The present disclosure is broadly directed to a chemical composition and method of applying same. More specifically, the present invention concerns the protection of a carved pumpkin, by immersion of said carved pumpkin in the chemical composition operative to retard environmental degradation so as to prolong the useful life thereof.

A. Chemical Composition

Fungi and more particularly, mold will grow on carved pumpkins. This mold growth is both unsightly and potentially dangerous. Allowing mold to grow unchecked can have serious health risks, causing allergic reactions, asthma episodes, infections, and other respiratory problems in humans.

Decay mold and decay fungi, both of which contribute to decomposition of plant material, have approximately a neutral pH level (pH 6-7.5). Raising or lowering pH levels beyond this range will prohibit the growth of most of these organisms, but compost microorganisms operate best under neutral to acidic conditions (pH 5.5-8). During the initial stages of decomposition, organic acids are formed. The acidic conditions are favorable for cellulolysis (breakdown) of cellulose and lignin in the plant. The primary cell walls of green plants, which are made of cellulose, are the primary structural component of the plant. The secondary cell wall contains cellulose with various amounts of lignin, which is an organic polymer conferring mechanical strength to the cell wall and by extension the plant as a whole. Weakening of the mechanical strength of the plant will result in undesirable softening, geometric distortions and collapse of the carved pumpkin.

It is therefore desirable to increase pH (reduce acidity), retard cellulolysis and retard the growth of fungi of carved pumpkins, and due to the fact that carved pumpkins are intended to be handled by children, it is advantageous to use a natural fungicide. The preferred element for increasing pH (lowering acidity), retarding cellulolysis and retarding growth of fungi on carved pumpkins is calcium hydroxide.

Since chemical reaction between carved pumpkins and the calcium hydroxide will over time reduce the pH level of the solution, it is advantageous to incorporate a pH buffer, to resist change in the pH level and maintain the effectiveness of the calcium hydroxide. The preferred pH buffer element is a compound selected from the group consisting of sodium tetraborate pentahydrate and sodium tetraborate decahydrate.

Bacteria are mostly responsible for the decomposition of carved pumpkins. It is this bacterial decomposition that raises the pH levels mentioned above, while breaking down the long molecular chains of complex carbohydrates, proteins, and lipids that comprise organic materials. Additionally, larger organisms such as insects are attracted to these complex carbohydrates, proteins, and lipids contained within the carved pumpkin, and will consume it. While the health and safety risks of insect infestation of carved pumpkins are negligible, the psychological and emotional effects of insect infestation, especially in children, can be devastating. Also, the consumption of the carved pumpkin by insects further contributes to the collapsing or other geometric distortions of the carved pumpkin.

It is therefore desirable to retard the growth of bacteria and repel insects in a way that is safe for both the environment and humans, especially children, handling the carved pumpkin. The preferred antiseptic (anti-bacterial) and insecticidal element is a compound selected from the group consisting of sodium tetraborate pentahydrate and sodium tetraborate decahydrate.

Bacteria, decay mold and decay fungi are present in almost all organic materials. Carved pumpkins also contain relatively large volumes of water within their cells. When moisture and a food source (namely the carved pumpkin) become available they will multiply rapidly. To retard the growth of microorganisms, carved pumpkins can be subjected to various dehydration methods. Unfortunately, it is the volume of water within the plant's cells, in addition to cellulose that gives plants their shape. Additionally, during the natural process of dehydration, carved pumpkins, will shrivel, collapse or experience other undesirable geometric distortions.

Temperature changes also have serious effects on the length of time carved pumpkins may be displayed. In addition to supporting microbial growth, warm temperatures cause a "cooking" effect, softening the carved pumpkin, thus causing geometric distortions. Extreme cold temperatures cause water molecules within the plant's cells to freeze, creating ice crystals which expand and destroy the plant's cells. Repeated freezing and thawing cycles will quickly break down the structure of the carved pumpkin and cause the pumpkin to collapse within a few days.

It is therefore desirable to remove the moisture from the carved pumpkin cells and replace it with another substance to maintain structural integrity which is also impervious to decay, such as a mineral, thus preserving the shape of the carved pumpkin without contributing to the growth of microorganisms. The preferred element for removing moisture from carved pumpkins and replacing said moisture with a mineral, namely calcium, is calcium hydroxide.

The preferred embodiment of the chemical composition is illustrated by Table 1, as follows:

TABLE 1

| Chemical Substance | Weight % |
| --- | --- |
| Calcium Hydroxide | 3 |
| Compound selected from the group consisting of Sodium Tetraborate Pentahydrate and Sodium Tetraborate Decahydrate | 2 |
| Water | 95 |

The order in which the elements are combined to form the chemical composition is inconsequential, provided the proper ratios of elements are maintained. For example, the calcium hydroxide may be added to the sodium tetraborate, with this mixture then being added to water to form an aqueous solution. This represents the most convenient method of formulation, in that the calcium hydroxide and sodium tetraborate is provided to the consumer as a dry mixture, to which the consumer adds water.

Additionally, several other mixing procedures may be used, including but not limited to, mixing one or all components in water, then adding additional components.

B. Method of Application

In living plants, water from the soil is distributed to specific areas in the plant through the plant's xylem, which consists of tracheas, which are dead hard-walled cells arranged to form tiny tubes to function in water transport. Before harvesting, the plant is able to move water from the roots to the upper extents of the plant through the xylem using the transpiration process, which is a result of the decrease in hydrostatic (water) pressure in the upper parts of the plants due to the diffusion of water out of stomata into the atmosphere, thus drawing the water upward from the roots. These xylem tubes are ideal for transporting preservative solution throughout the inner structures of carved pumpkins, but the harvesting, cleaning, and carving of the plant destroys the natural transpiration process. If preservative solutions are applied only to the surface of the carved pumpkin, they are only effective on the outside surfaces of the carved pumpkin. If however the carved pumpkin is immersed in a solution, hydrostatic pressures can be created, thus transporting the immersion solution containing the preservative throughout the inner structures of the carved pumpkin via the plant's xylem.

For example, carved pumpkins placed 30 centimeters (approximately twelve inches) below the surface of water will experience a hydrostatic pressure of 2,940 pascals. As the pumpkin is placed deeper (further below the surface of the water), the hydrostatic pressure increases 98.1 pascals every centimeter. Also, solutions with densities greater than water will produce greater hydrostatic pressures. Therefore it is advantageous to utilize hydrostatic pressure to force preservatives throughout the inner structures of the carved pumpkin. The preferred method for creating hydrostatic pressure is to completely immerse the carved pumpkin in an aqueous solution containing preservative elements, for a time period of no less than four hours, and no more than twenty four hours.

While immersion of the carved pumpkin in the aqueous solution represents the preferred and most effective means of application, topical application of the solution in the form of spraying, brushing or other means have demonstrated positive results.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A method of preserving a carved pumpkin consisting of:
   treating the carved pumpkin with a composition consisting essentially of water,
   a hyperosmotic amount of an alkaline material, and
   a buffer for maintaining pH above 8.0,
   wherein the buffer is selected from the group consisting of sodium tetraborate pentahydrate and sodium tetraborate decahydrate, and
   wherein the composition has fungicidal properties, removes moisture from the carved pumpkin, adds mineral content to the carved pumpkin, retards bacterial growth, and/or repels insects.

2. The method of claim 1, wherein said alkaline material comprises a weight percentage of between 1.0 and 3.0 percent of calcium hydroxide.

3. The method of claim 1, wherein the buffer for maintaining pH levels above 8.0, is between 0.1 and 2.0 weight percent of a compound selected from the group consisting of sodium tetraborate pentahydrate and sodium tetraborate decahydrate.

4. The method of claim 1, wherein said treating step is total immersion of the carved pumpkin in the composition for no less than four hours and no more than twenty-four hours.

5. An aqueous composition for preserving a carved pumpkin, for preventing environmental degradation and repelling insects, consisting essentially of:
   a weight percentage of between 1.0 and 3.0 percent of calcium hydroxide, for raising pH, providing fungicidal properties, removing moisture and adding mineral content;
   a weight percentage of between 0.1 and 2.0 percent of a compound selected from the group consisting of sodium tetraborate pentahydrate and sodium tetraborate decahydrate, for providing a buffer to maintain pH levels above 8.0, retard bacterial growth and repel insects; and
   the balance water.

6. A kit for preserving a carved pumpkin, for preventing environmental degradation and repelling insects, consisting essentially of: between 1.0 and 3.0 parts of calcium hydroxide, for raising pH, providing fungicidal properties, removing moisture and adding mineral content; between 0.1 and 2.0 parts of a compound selected from the group consisting of sodium tetraborate pentahydrate and sodium tetraborate decahydrate, for providing a buffer to maintain pH levels above 8.0, retarding bacterial growth and repelling insects; and
   an instruction to the consumer to add 95 to 98.9 parts water.

\* \* \* \* \*